US008834528B2

(12) United States Patent
Anderson et al.

(10) Patent No.: US 8,834,528 B2
(45) Date of Patent: Sep. 16, 2014

(54) SPINAL FIXATION DEVICE AND TECHNIQUE FOR EXPANSION OF THE SPINAL CANAL

(76) Inventors: D. Greg Anderson, Moorestown, NJ (US); Steven Craig Ludwig, Baltimore, MD (US)

(*) Notice: Subject to any disclaimer, the term of this patent is extended or adjusted under 35 U.S.C. 154(b) by 416 days.

(21) Appl. No.: 13/021,334

(22) Filed: Feb. 4, 2011

(65) Prior Publication Data

US 2011/0270317 A1 Nov. 3, 2011

Related U.S. Application Data

(60) Provisional application No. 61/301,809, filed on Feb. 5, 2010.

(51) Int. Cl.
*A61B 17/70* (2006.01)
(52) U.S. Cl.
CPC ......... *A61B 17/7071* (2013.01); *A61B 17/7067* (2013.01)
USPC ........................................... 606/279; 606/246
(58) Field of Classification Search
CPC ......... A61B 17/56; A61B 17/70; A61B 17/88
USPC ................. 606/246–253, 256–260, 264–272, 606/276–279, 301, 90, 105
See application file for complete search history.

(56) References Cited

U.S. PATENT DOCUMENTS

| | | | | |
|---|---|---|---|---|
| 3,242,922 A | * | 3/1966 | Thomas | 606/250 |
| 6,358,254 B1 | * | 3/2002 | Anderson | 606/103 |
| 6,428,540 B1 | * | 8/2002 | Claes et al. | 606/53 |
| 7,166,107 B2 | * | 1/2007 | Anderson | 606/86 A |
| 7,611,526 B2 | * | 11/2009 | Carl et al. | 606/248 |

* cited by examiner

*Primary Examiner* — Pedro Philogene
*Assistant Examiner* — David Comstock
(74) *Attorney, Agent, or Firm* — Blank Rome LLP

(57) ABSTRACT

A fixation device expands the spinal canal through osteotomies of the dorsal spinal elements (e.g lamina). Fixation is established to the dorsal vertebral elements (e.g. spinous process or lamina), with connection to a fixation device on each side of respective osteotomies. A distracting mechanism dorsally translates the fixated dorsal vertebral elements to expand the spinal canal. The fixation device allows secure fixation of the vertebra in the expanded state to promote bony healing across the osteotomy site. The fixation device can include a dorsal vertebral device (e.g., a transosseous fixation member placed through the spinous process) connected to a vertebral fixation device (e.g., bone screw or rod) by a connecting device with distracting mechanism. The connecting device spans the respective osteotomy, includes the distracting mechanism, and translates (lifts) the dorsal vertebral device from the vertebral fixation device in a dorsal direction to promote spinal canal expansion.

29 Claims, 9 Drawing Sheets

SPINAL FIXATION DEVICE AND TECHNIQUE FOR EXPANSION OF THE SPINAL CANAL

RELATED APPLICATIONS

The application claims benefit of priority of U.S. Provisional Application No. 61/301,809, filed Feb. 5, 2010. U.S. Provisional Application No. 61/301,809, is incorporated herein by reference.

FIELD OF THE INVENTION

The present invention relates generally to the field of spinal surgery and more particularly to treatments for spinal stenosis and spinal fixation for fusion and non-fusion treatments of the spine.

BACKGROUND OF THE INVENTION

Spinal stenosis is a disease involving narrowing of the spinal canal leading to compression of the spinal cord and/or nerve roots. Depending on the location and severity of the spinal stenosis, this condition may lead to neurologic dysfunction including weakness, numbness, balance problems, problems walking, loss of coordination and loss of hand function. In particular, spinal stenosis of the cervical region is a common cause of major neurologic dysfunction resulting from compression of the spinal cord.

Traditional treatments for spinal stenosis involve surgical decompression of the spinal cord from either an anterior, posterior or combined surgical approach. Due to the invasive nature of these operations, the risks and benefits of surgery for spinal stenosis must be carefully weighed by patients and physicians considering this form of intervention. A laminectomy is the most common type of surgery employed for multilevel spinal stenosis and this operation may produce major bleeding, scarring, muscle damage and/or spinal instability in some patients undergoing this type of surgery. Although minimally invasive options have been devised for many spinal conditions, no well accepted minimally invasive options have yet been described for the treatment of spinal stenosis affecting the cervical or thoracic area. For all these reasons, there is a strong need for a novel technique to treat spinal stenosis in a less invasive fashion, sparing the normal anatomic structures and lessening the risks of spinal surgery.

SUMMARY OF THE INVENTION

The present invention provides a method and a spinal canal expansion device to correct spinal stenosis by a minimally invasive technique that lessens the risk of bleeding, scarring, muscle damage and spinal instability inherent in current techniques. In one aspect of the invention, a spinal canal is expanded by establishing implant fixation of dorsal vertebral elements, cutting a vertebra in two locations to separate the dorsal vertebral elements from a remainder of the vertebra, establishing implant fixation of the remainder of the vertebra, and separating the dorsal spinal elements of the vertebra from the remainder of the vertebra, through use of the spinal canal expansion device, to expand the spinal canal. Separation involves use of a distracting mechanism, communicating with each of the fixated dorsal vertebral elements and the fixated remainder of the vertebra, to elevate the dorsal vertebral elements from the remainder of the vertebra.

Embodiments of the present invention will be seen variously to:

lessen the size of the incisions necessary to perform spinal decompression;
avoid removing normal portions of the spinal column, such as the lamina and spinous process;
lessen the risk of bleeding or scarring inherent in traditional spinal decompression surgery;
lessen the risk of spinal instability following spinal decompression surgery;
allow spinal decompression to be achieved by a minimally invasive technique;
improve lordosis of the cervical or lumbar region during the spinal decompression procedure; and
provide fixation for a spinal fusion procedure if needed during the spinal decompression procedure.

In one aspect of the invention, a method for correcting spinal stenosis involves expanding the spinal canal by cutting the spinal lamina bilaterally and using spinal implant(s) to elevate the spinous process and lamina away from the spinal cord and nerve sac, thus decompressing the spinal canal. In another aspect of the invention, the spinal canal expansion device used for correcting spinal stenosis includes expandable linkage to both elevate the lamina and spinous process, and to fixate the vertebra in the expanded state using a stabilizing bar attached to the spinous process. In another aspect, suboptimal lordosis of the spine can be corrected by the action of the spinal canal expansion device, which imparts an anteriorly-directed force vector to the vertebral body that improves lordosis of the treated spinal segment.

Generally, the spinal canal expansion device of the present invention includes a dorsal vertebral device connected to a dorsal vertebral element of the vertebra, a vertebral fixation device connected to a vertebral element more anterior than the dorsal vertebral element, and a connecting device. The connecting device generally provides communication between the dorsal vertebral device and the vertebral fixation device. In use, the connecting device spans a dorsal vertebral osteotomy, and includes a distracting mechanism operating to translate the dorsal vertebral element, via anteriorly-directed force, in a dorsal direction relative to the more anterior vertebral element. The dorsal vertebral osteotomy is thereby separated resulting in expansion of the spinal canal.

The present invention has multiple advantages over current known methods and implants for treating spinal stenosis:
(1) The maintenance of normal anatomic structures including the spinous process, lamina and muscles of the dorsal spine;
(2) The ability to correct spinal stenosis with a minimally invasive procedure;
(3) The ability to provide secure fixation for healing of the spine in the expanded state;
(4) The ability to provide secure fixation for treating coexistent spinal stenosis;
(5) The ability to minimize bleeding, scaring, muscle damage and risk of instability following surgery; and
(6) The ability to improve spinal lordosis.

BRIEF DESCRIPTION OF THE DRAWINGS

The drawings herein are included for the purpose of illustrating preferred embodiments of the present inventions; however, it should be realized that the invention is not limited to the precise arrangements and/or sequence of steps shown.

DETAILED DESCRIPTION OF THE ILLUSTRATED EMBODIMENTS

Figure 1:
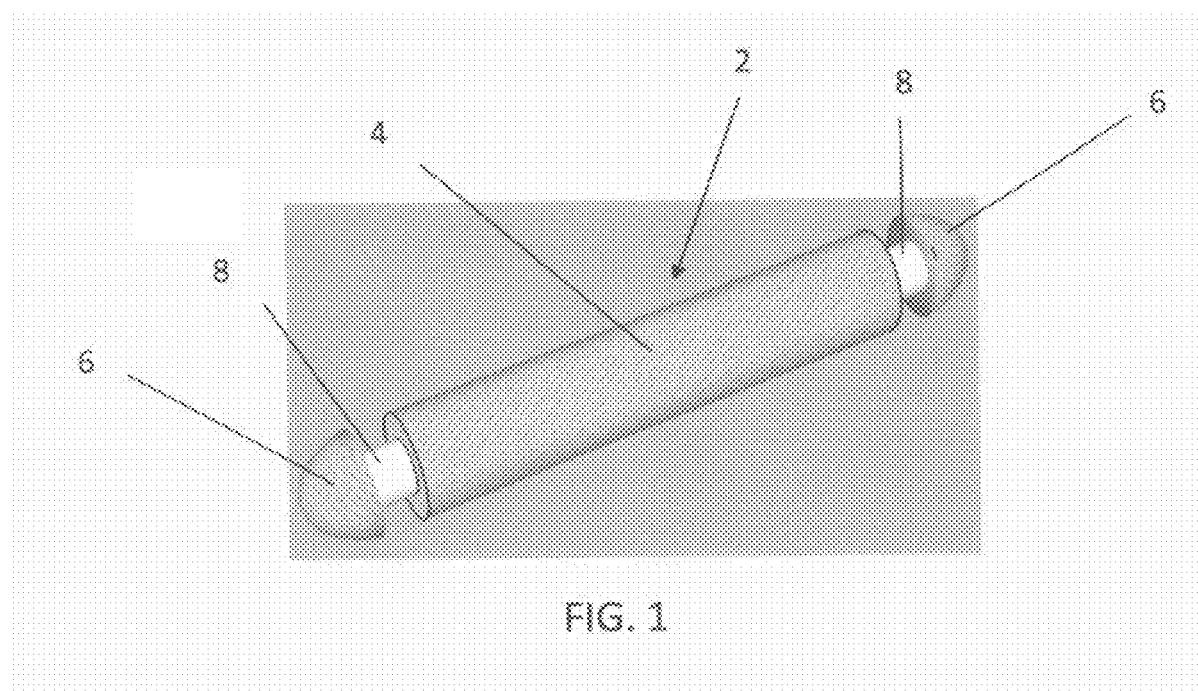
FIG. 1 illustrates a perspective view of a transosseous fixation component.
Figure 2A:
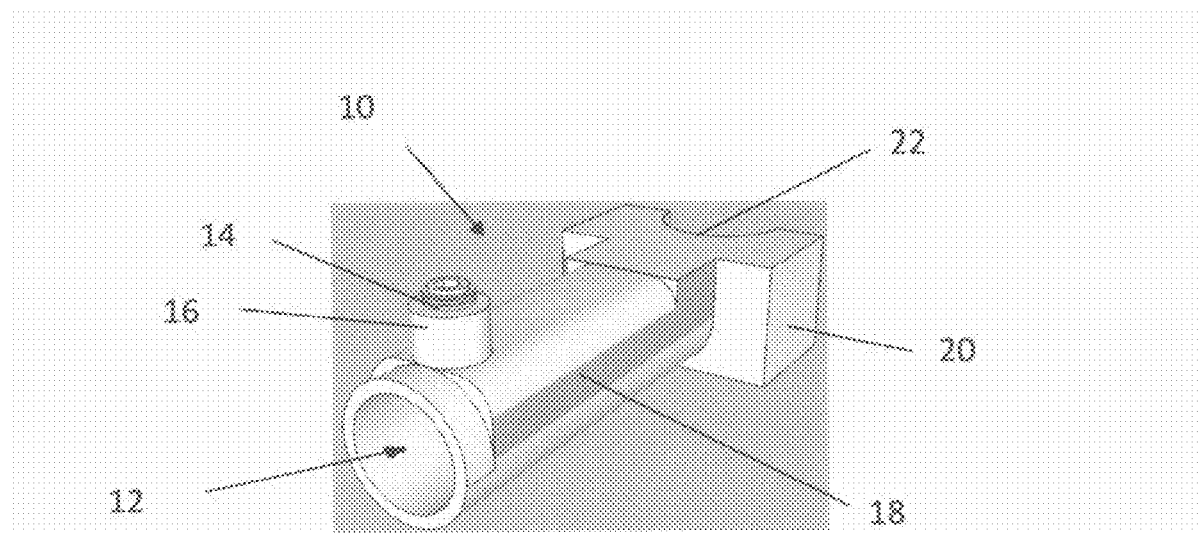
FIGS. 2a and 2b illustrate perspective views of an adjustable connector.

Referring now to the drawings, wherein like numerals indicate like elements, there is shown in FIG. 1 an embodiment of a dorsal vertebral device for implant fixation to dorsal vertebral elements. More specifically, the embodiment shown in FIG. 1 is involves a transosseous fixation member 2, which comprises a shaft 4 designed to pass through a transosseous bone tunnel. On each end of the shaft 4 is a connecting member 6, which allows the transosseous fixation member 2 to be attached to a connecting device of the present invention (e.g., an adjustable connector 10 of FIG. 2a). Note that, in this preferred embodiment, the connecting member 6 has rounded ends to accommodate various angular arrangements between the dorsal vertebral device (or transosseous fixation member 2) and the adjustable connector 10 (FIG. 2a). Also seen in the transosseous fixation member 2 are fixation grooves 8 which allow for fixation bolts 14 (FIG. 2a) of the adjustable connector 10 to secure the connection of the transosseous fixation member 2 and the adjustable connector 10 (FIG. 2a).

Figure 2B:
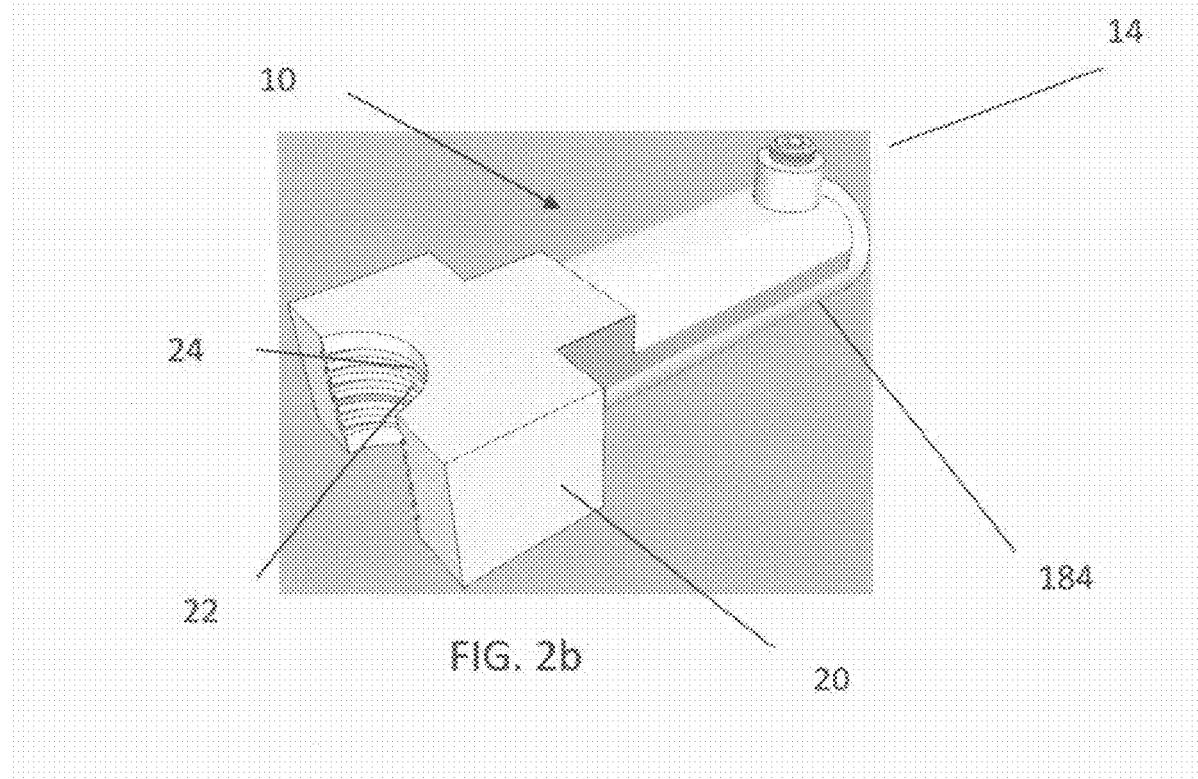

FIGS. 2a and 2b illustrate one embodiment of a component of a connecting device of the present invention. The embodiment of FIGS. 2a and 2b specifically illustrate the adjustable connector 10, which comprises a connecting tube 18 and sliding section 20. The connecting tube 18 comprises an opening 12 for transosseous fixation member 2 (FIG. 1) and a fixation bolt 14, threadably attached to a bolt anchorage 16, which is capable of securing the connection between the adjustable connector 10 and the transosseous fixation member 2 (FIG. 1). The sliding section 20, comprises an internally threaded groove 22 with internal threads 24 designed to mate with the threads 33 of a jack screw 32 (FIGS. 3a & 3b).

Figure 3A:
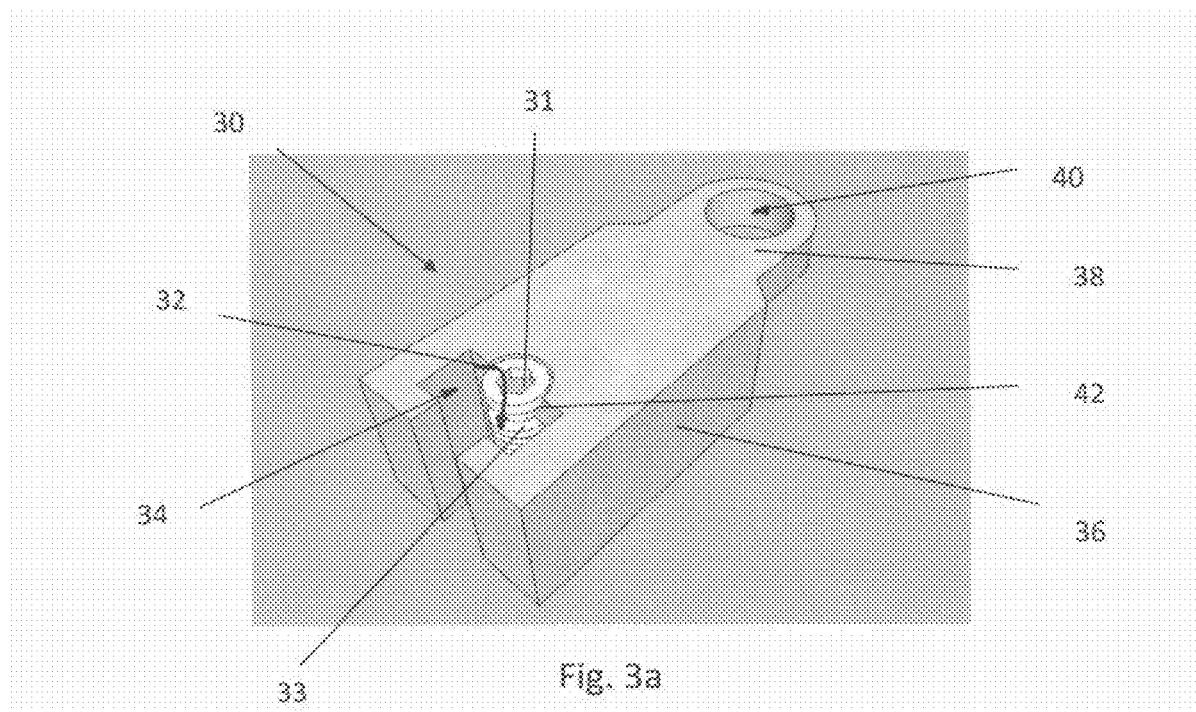
FIGS. 3a and 3b illustrates perspective views of a jack component.
Figure 3B:
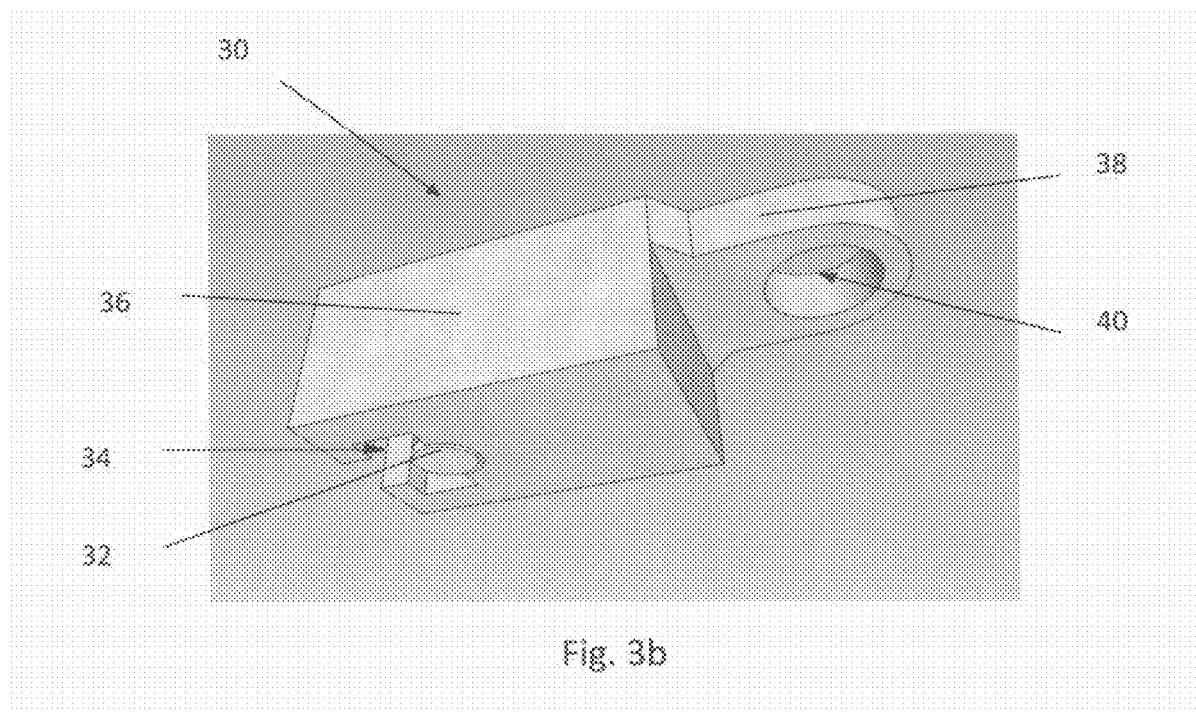
Figure 4A:
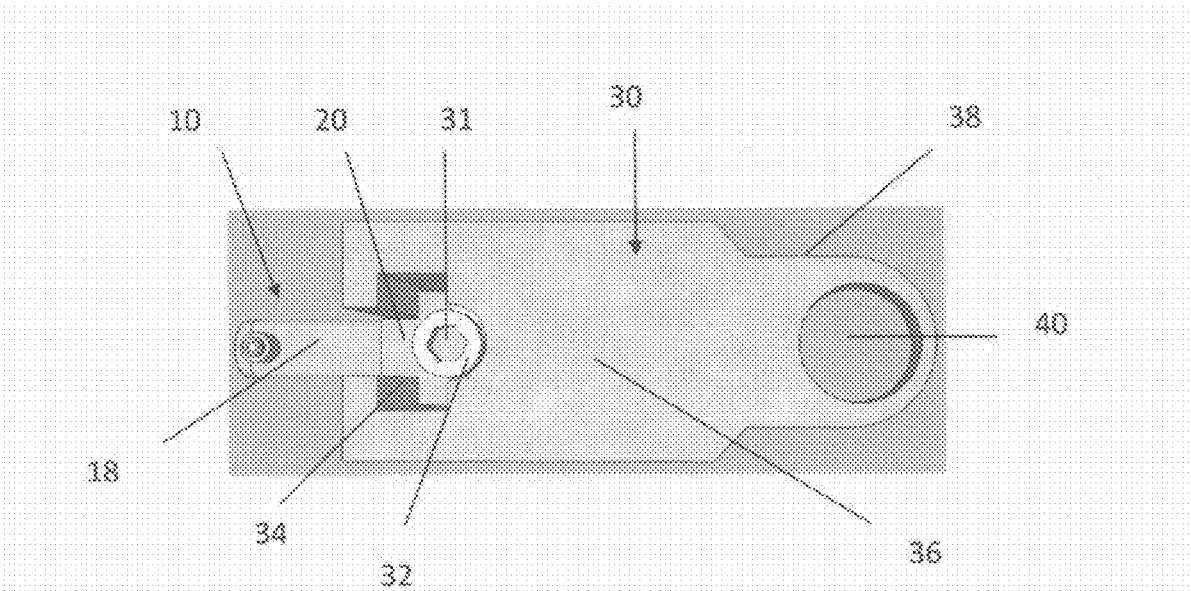
FIGS. 4a and 4b illustrates perspective views of the assembly of the adjustable connector and the jack component.
Figure 4B:
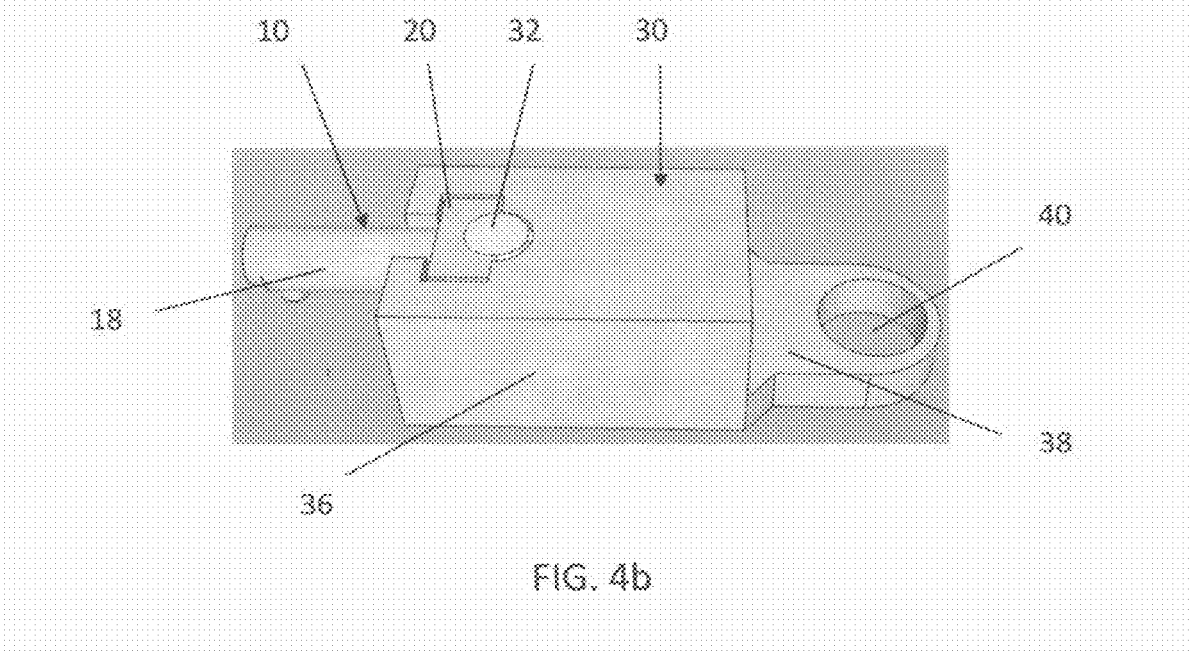
Figure 5:
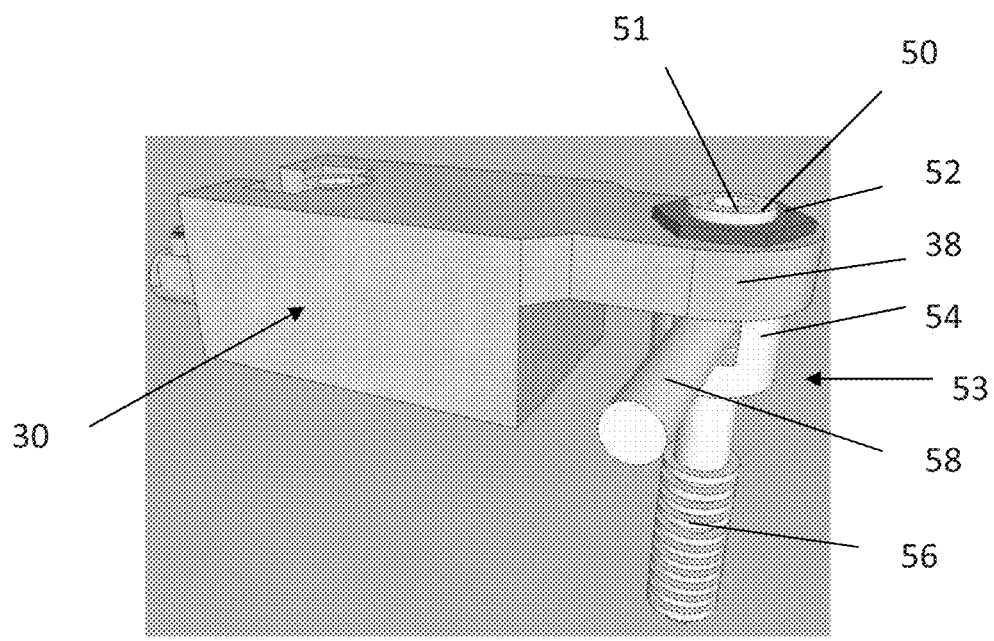
FIG. 5 illustrates a perspective view of the attachment of the assembled adjustable connector and jack component to a bone screw assembly.

FIGS. 3a and 3b illustrate prospective views of one embodiment of another component of the connecting device of the present invention. The embodiment of FIGS. 3a and 3b specifically illustrate a jack component 30, which comprises a body portion 36, a fixation tab 38, an elevation slot 34 and a jack screw 32 having a driver mechanism 31. The fixation tab 38 comprises a fixation bore 40, allowing connection of the jack component 30 to a bone screw 53 (FIG. 5). The elevation slot 34 includes therein an integrated jack screw 32 connected to the body portion 36 by a retention mechanism 42. The elevation slot 34 has a shape that is substantially complimentary to the sliding section 20 of the adjustable connector 10 (FIGS. 2a & 2b) for reception of the sliding section 20 within elevation slot (FIGS. 4a & 4b). The jack screw 32 contains threads 33 which threadably mate with the internally threaded groove 22 of the adjustable connector 10 (FIGS. 2a & 2b).

FIGS. 4a and 4b illustrate perspective views of an assembled adjustable connector 10 and jack component 30, together illustrating one embodiment of a distracting mechanism of the connecting device of the present invention. Note that the sliding section 20 of the adjustable connector 10 fits into the elevation slot 34 of the jack component 30. Jack screw 32 threadably engages the internally threaded grooves 22 of the sliding section 20 such that rotation of the jack screw 32 via the driver mechanism 31 will result in up or down (translational) movement of the sliding section 20 within the elevation slot 34. Also, note the location of the connecting tube 18, designed to attach to the transosseous fixation component 2 (of FIG. 1), and the fixation tab 38 and fixation bore 40, designed to attach to a bone screw 53 (shown in FIG. 5).

FIG. 5 is a perspective view of a connection of the jack component 30 to one embodiment of a vertebral fixation device of the present invention. Note also that in FIG. 5 the jack component 30 is shown assembled to the adjustable connector 10. The embodiment of FIG. 5 specifically illustrates a bone screw 53. The bone screw 53 includes a head 54, a shaft 56 and an attached rod 58. The bone screw 53 is attached to the fixation tab 38 of the jack component 30 by an elongated locking bolt 50 on the bone screw 53 that projects through the bore 40 (FIGS. 4a & 4b) of the fixation tab 38. The elongated locking bolt 50 is then captured by a locking nut 52, which upon tightening securely connects the jack component 30 to the bone screw 53.

More specifically, in one embodiment, the elongated locking bolt 50 threads down (internally) into the bone screw 53, via tightening mechanism 51, to secure the rod 58 within a hole in the head 54 of the bone screw 53. Otherwise, the rod 58 is capable of sliding within the hole in the head 54 of the bone screw 53. The bore 40 of the fixation tab 38 fits over the locking bolt 50 with a slightly loose connection. The locking nut 52 then threads onto the locking bolt 50 and is tightened to compress against, and thus secure, the fixation tab 38 to the bone screw 53.

Figure 6:
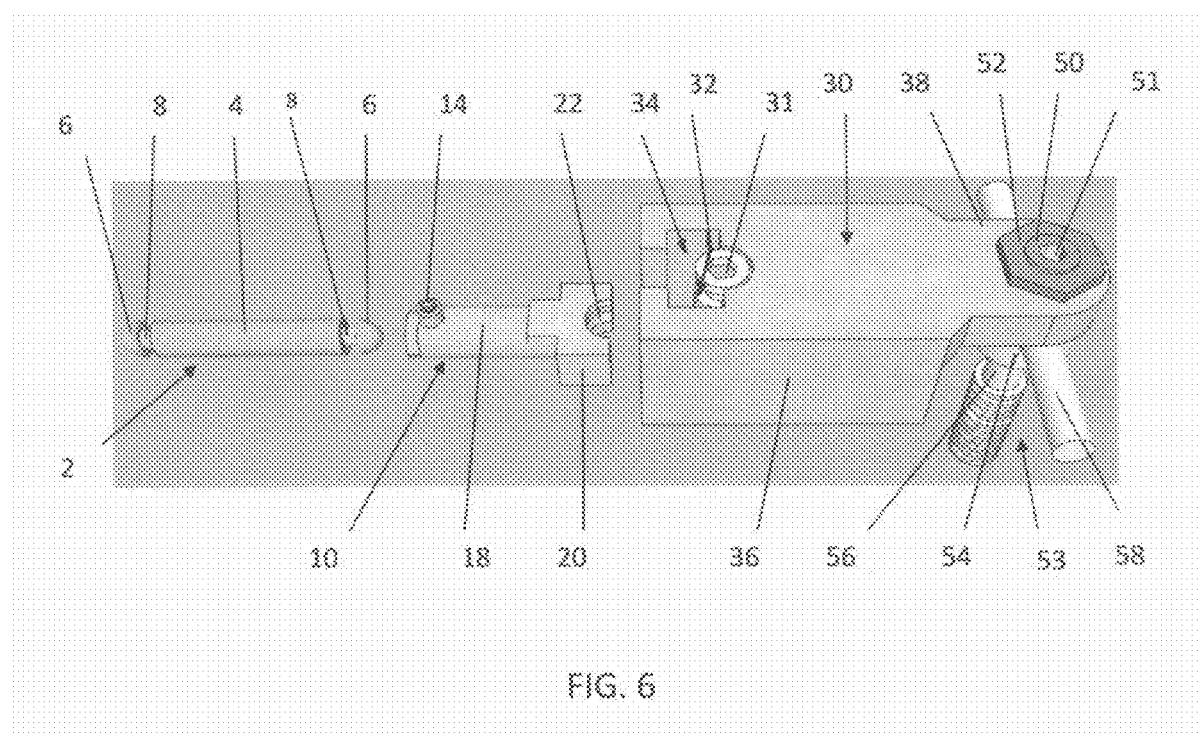
FIG. 6 illustrates an exploded perspective view of a spinal canal expansion device.

FIG. 6 illustrates an exploded perspective view of components of certain embodiments of the present invention. More generally, FIG. 6 illustrates specific embodiments of the dorsal vertebral device, the connecting device with distracting mechanism, and the vertebral fixation device. More specifically, FIG. 6 illustrates embodiments including the transosseous fixation member 2, the adjustable connector 10, the jack component 30 (with jack screw 32), and the bone screw 53 assembly. In this illustrated embodiment, note the relationship between the various components, including the connecting member 6 of the transosseous fixation member 2, which connects to the connecting tube 18 of the adjustable connector 10. Also note that the sliding section 20 of the adjustable connector 10 is inserted into the elevation slot 34 of the jack component 30, bringing the internally threaded groove 22 into contact with the jack screw threads 33 of the jack screw 32. The action of the jack screw threads 33, relative to the internally threaded grooves 22, is exerted through the rotatable motion of the jack screw 32 via the driver mechanism 31, producing a vertical change in the position of (or a translation of) the sliding section 20 of the adjustable connector 10 within (and relative to) the elevation slot 34 of the jack component 30.

Figure 7A:
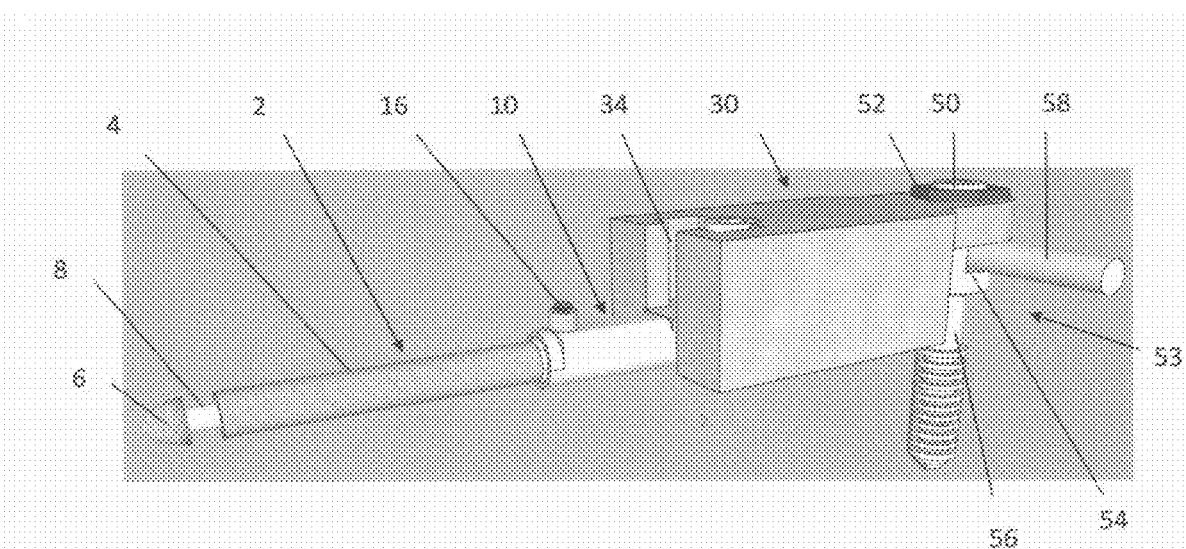
FIGS. 7a and 7b illustrate perspective views of the spinal canal expansion device in un-raised (FIG. 7a) and raised (FIG. 7b) positions.
Figure 7B:
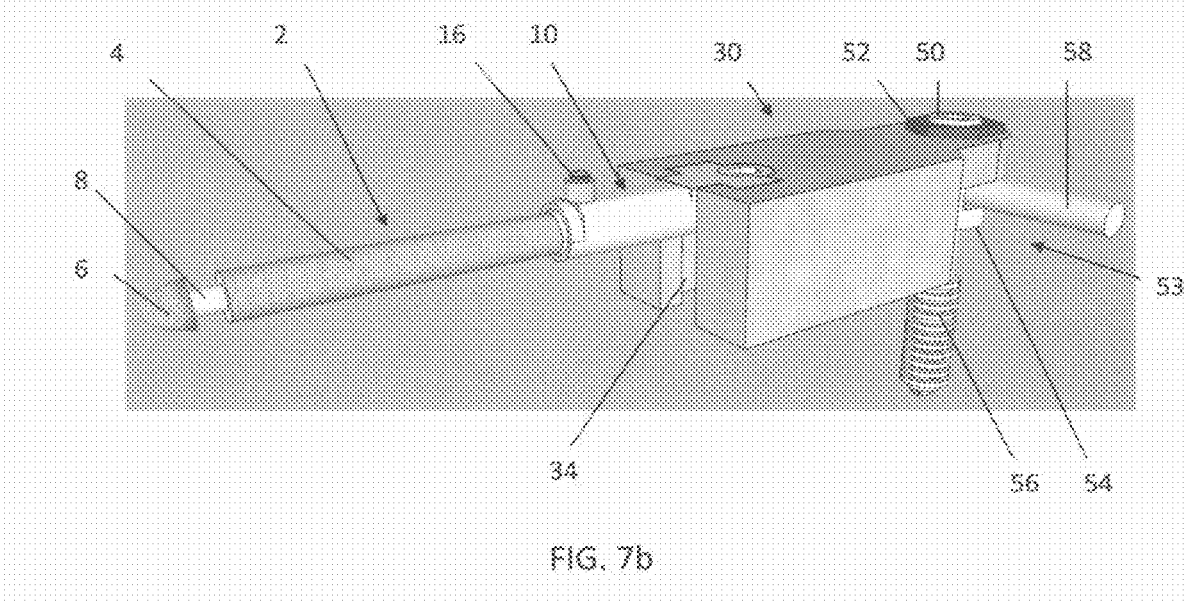

FIGS. 7a and 7b illustrate perspective views of an embodiment of the spinal canal expansion device, with distracting mechanism in an un-raised (FIG. 7a) and a raised (FIG. 7b) positions. Note, in this specifically illustrated embodiment, that the transosseous fixation member 2 is attached to the adjustable connector 10, which is attached to the jack component 30. In FIG. 7a, the adjustable connector 10 is in the un-raised position, defined as when the adjustable connector 10 is located in the lower portion of the elevation slot 34 of the jack component 30. In FIG. 7b, the adjustable connector 10 is in the raised position, defined as when the adjustable connector 10 is in the upper portion of the elevation slot 34 of the jack component 30.

Figure 8:
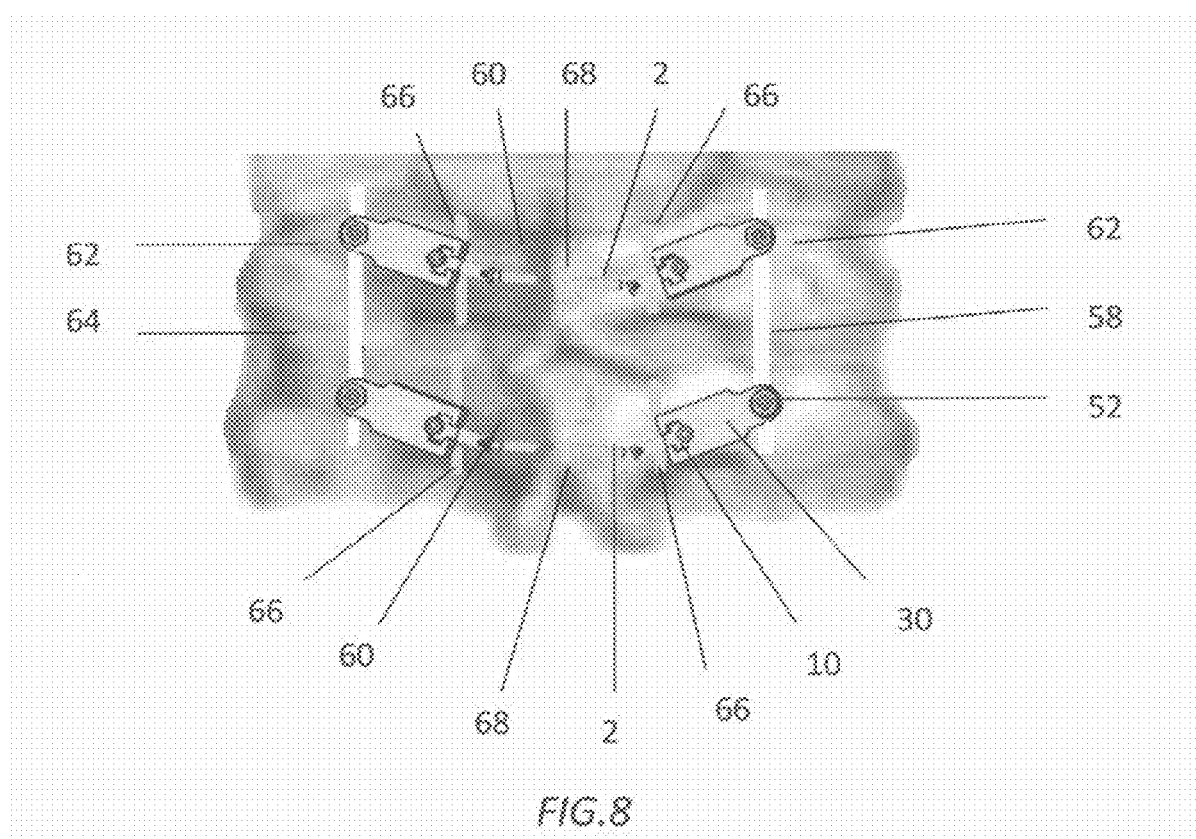
FIG. 8 illustrates a dorsal view of the spinal canal expansion device attached to the cervical spine at two contiguous levels.

FIG. 8 illustrates a dorsal view of the posterior cervical spine with embodiments of the spinal canal fixation device implanted at two contiguous vertebral levels. In this specifically illustrated embodiment, note the two transosseous fixation members 2, each respectfully inserted through a spinous process 68 of adjacent vertebra. The transosseous fixation members 2 are each seen attached, at each end, to adjustable connectors 10, which are each attached to a jack component 30. Each jack component 30, in turn, is respectfully attached to a bone screw 53 via locking nuts 52 (see FIGS. 5-7). The bone screws 53 (FIGS. 5-7) are attached, or fixed, to one another (across contiguous vertebral levels) by rods 58. The bone screws 53 are inserted (threaded) into the lateral masses 62 of the two vertebral levels. Referring to FIGS. 8-9, an osteotomy (bone cut) 66 is seen through the lamina 60 on each side of the vertebra at both vertebral levels. The osteotomy (bone cut) 66 separates the medial (midline) portion of the lamina 60 and spinous process 68 from the lateral portion of the lamina 60 and the lateral masses 62. It is understood that aspects of the present invention provide for osteotomies in varying vertebral location.

Figure 9A:
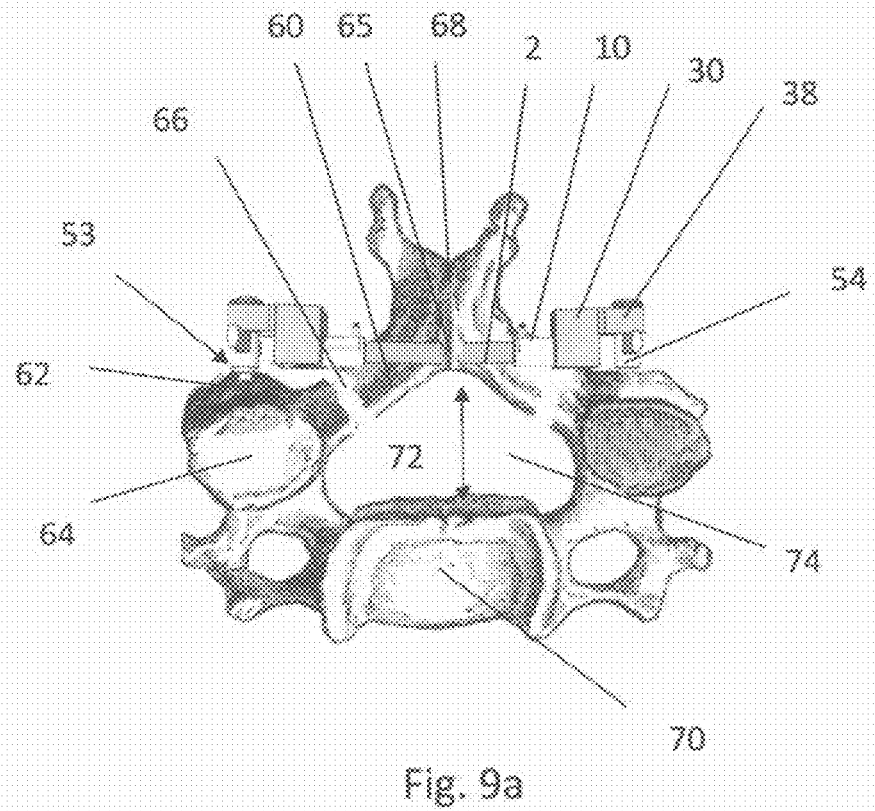
FIGS. 9a and 9b illustrate the action of the spinal canal expansion device on the spinal lamina, showing expansion of the spinal canal by the dorsal movement of the spinal lamina through the action for the spinal canal expansion device.
Figure 9B:
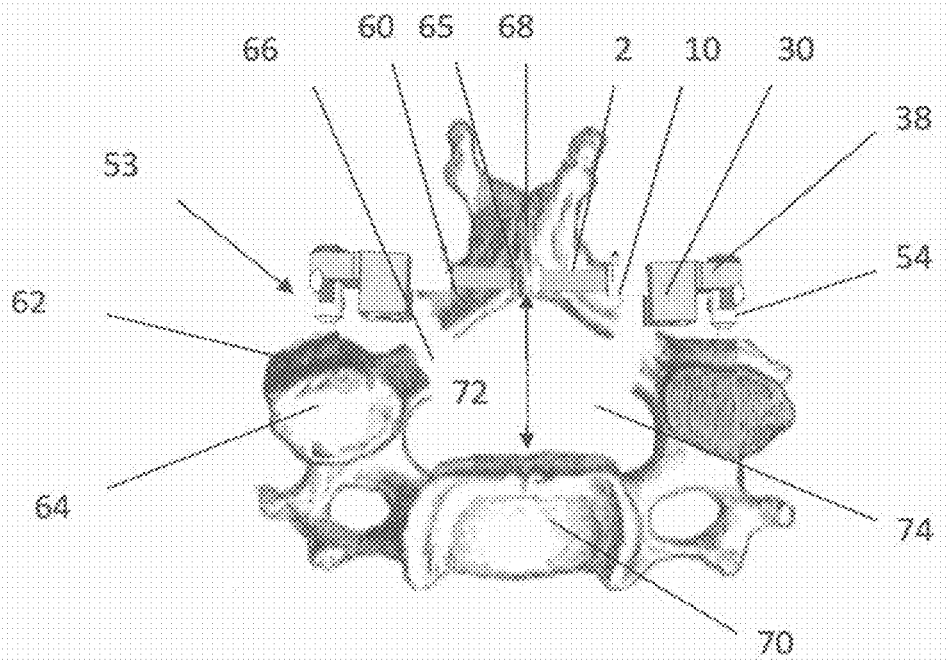

FIGS. 9a and 9b illustrate the action of an embodiment of the spinal canal expansion device to expand the spinal canal 74. The transosseous fixation member 2 is seen traversing a bone bore 65 at the base of the spinous process 68. Bone screws 53 are seen anchored into the lateral masses 62, bilaterally. Osteotomies (bone cuts) 66 are seen dividing the lamina 60 bilaterally. In FIG. 9a, the illustrated spinal canal expansion device is seen in the un-raised position, with the spinal canal sagittal diameter 72 at a baseline (pre-treatment) diameter. In FIG. 9b, the illustrated spinal canal expansion device is seen in the raised position, causing the lamina 60 and the spinous process 68 to be translated in a posterior direction, thereby increasing the spinal canal sagittal diameter 72 and expanding the cross sectional area of the spinal canal 74. Note that in FIG. 9b, the adjustable connector 10 is in a more dorsal position, relative to the jack component 30, and relative to that shown in FIG. 9a.

Methods of the Present Invention and Methods of Use of the Illustrated Embodiments Methods of the present invention involve establishing implant fixation of dorsal vertebral elements. In one specific embodiment, a bore 65 is drilled across a ventral portion of the spinous process 68, followed by placement of the transosseous fixation member 2 into and through the bore 65.

An osteotomy (bone cut) 66 is made, preferably in two locations, to separate the dorsal vertebral elements from a remainder of the vertebra. In one specific embodiment, osteotomies 66 are made in two locations, each along a lamina 60, on both sides of the vertebra, using techniques well known in the art of spinal surgery. The osteotomies (bone cuts) 66 are preferably made substantially along the lateral margins of the spinal cord.

Vertebral fixation devices are connected to vertebral elements more anterior than the dorsal vertebral element above. In one specific embodiment, bone fixation screws 53 are placed (threaded) into lateral masses 62 on each side of a vertebra, using techniques well known in the art of spinal surgery. Note that the bone screws 53 may be connected to one another by rods 58, when a spinal fusion is desired, or may be used without rods 58 when no fusion is desired.

A size of the connecting device and/or distracting mechanism can be adapted to the size of the patient. In a specific embodiment, the jack component 30 and the sliding section 20 size is preferably selected by measuring a distance between the end of the transosseous fixation rod 2 and the respective screw head 54. An appropriately sized jack component 30 and sliding section 20 are selected to accommodate this distance.

The various components are connected; that is, the dorsal vertebral device, the vertebral fixation device, and the connecting device. In one specific embodiment, the assembled jack component 30 and adjustable connector 10 are preferably attached to a respective head 54 of the bone screw 53 by placing the fixation bore 40 of the fixation tab 38 over an elongated locking bolt 50, then threadably attaching and tightening a locking nut 52 to the locking bolt 50 of each bone screw 53. In addition, the connecting tube 18 is fit over the connection member 6 of the transosseous fixation rod 2; then the fixation bolt 14 is tightened to secure the connection of the adjustable connector 10 to the transosseous fixation rod 2. Recall that the connecting member 6 has rounded ends to allow angulation between the transosseous fixation member 2 and the adjustable connector 10, when connected (see FIG. 8). This allows the spinal canal fixation device to adjust to variations in the local anatomy of the spine.

To expand the spinal canal, in this embodiment, the jack screw 32 is turned (via driver mechanism 31) to elevate (raise) the sliding section 20 within the elevation slot 34 of the jack component 30. By this action, the transosseous fixation rod 2 moves in a dorsal direction, and elevates the attached spinous process 68 and lamina 60 portion, resulting in expansion of the spinal canal 72 (see FIGS. 9a and 9b).

What is claimed is:

1. A method for expanding and fixing a spinal canal, the method comprising the steps of:
   a. establishing implant fixation of dorsal vertebral elements;
   b. cutting a vertebra in two locations to separate the dorsal vertebral elements from a remainder of the vertebra;
   c. establishing implant fixation of the remainder of the vertebra; and
   d. separating the dorsal spinal elements of the vertebra from the remainder of the vertebra, to expand the spinal canal, by operating a distracting mechanism communicating with each of the fixed dorsal vertebral elements and the fixed remainder of the vertebra.

2. The method of claim 1, further comprising the step of securing the separation of the dorsal spinal elements from the remainder of the vertebra, across the vertebral cut, to promote healing of the vertebral cut with the spinal canal expanded.

3. The method of claim 1, wherein the vertebra is cut through the lamina.

4. The method of claim 1, wherein the dorsal vertebral elements include one or more of a spinous process, pars intraarticularis, lamina and articular processes.

5. The method of claim 1, wherein establishing implant fixation of the dorsal vertebral elements involves inserting a transosseous implant through the spinous process of the vertebra.

6. The method of claim 5, wherein the transosseous implant is connected to the distracting mechanism.

7. The method of claim 6, wherein the distracting mechanism is further connected to the implant fixed to the remainder of the vertebra.

8. The method of claim 7, wherein the implant fixed to the remainder of the vertebra is a bone anchorage mechanism.

9. The method of claim 8, wherein the bone anchorage mechanism is a bone screw, rod, plate, hook, wire, cable or nail.

10. The method of claim 6, wherein the distracting mechanism operates to elevate the transosseous implant.

11. The method of claim 10, wherein the distracting mechanism includes an adjustment mechanism, and operation of the adjustment mechanism elevates the transosseous implant, resulting in elevation of the spinous process, thereby expanding the spinal canal.

12. The method of claim 6, wherein connection of the distracting mechanism to the transosseous implant provides various angular arrangements during connection, thereby providing a plurality of positional adjustments between the distracting mechanism and the transosseous implant to accommodate variations in local spinal anatomy.

13. The method of claim 1, wherein establishing implant fixation of the remainder of the vertebra involves inserting a bone anchorage mechanism into a lateral mass of the vertebra.

14. The method of claim 13, wherein the bone anchorage mechanism is a bone screw, rod, plate, hook, wire, cable or nail.

15. The method of claim 13, wherein the bone anchorage mechanism is connected to the distracting mechanism.

16. The method of claim 15, wherein the distracting mechanism is further connected to the implant fixed to the dorsal vertebral elements.

17. The method of claim 16, wherein the distracting mechanism operates to elevate the implant fixed to the dorsal vertebral elements.

18. The method of claim 17, wherein the distracting mechanism includes an adjustment mechanism, and operation of the adjustment mechanism elevates the implant fixed to the dorsal vertebral elements, resulting in elevation of the spinous process and lamina, thereby expanding the spinal canal.

19. The method of claim 16, wherein connection of the distracting mechanism to the implant fixed to the dorsal vertebral elements provides various angular arrangements during connection, thereby providing a plurality of positional adjustments between the distracting mechanism and the implant fixed to the dorsal vertebral elements to accommodate variations in local spinal anatomy.

20. An implant for expanding and fixing a spinal canal, comprising:
a dorsal vertebral device that connects to a dorsal vertebral element of a first vertebra;
two vertebral fixation devices that each connect to a vertebral element of the first vertebra more anterior than the dorsal vertebral element;
two connecting devices, each connecting device providing communication between the dorsal vertebral device and a respective one of the two vertebral fixation devices, wherein:
a longitudinal axis of the dorsal vertebral device is aligned with a longitudinal axis of each connecting device;
each connecting device connected to the dorsal vertebral device, in use, spans a vertebral osteotomy in the first vertebra, and
each connecting device has a distracting mechanism with two sections that translate relative to one another along an axis generally perpendicular to the longitudinal axis of the respective connecting device, to translate the dorsal vertebral device in a dorsal direction relative to the respective one of the two vertebral fixation devices, whereby the vertebral osteotomies are separated to expand the spinal canal.

21. The implant of claim 20, wherein the dorsal vertebral device is a transosseous implant communicating with a spinous process of the first vertebra, the transosseous implant being shaft-like, passing through a tunnel formed in the spinous process.

22. The implant of claim 20, wherein the connecting device having a distracting mechanism with two sections includes:
a slot aligned generally perpendicularly to the longitudinal axis of the connecting device; and
a sliding section movable within the slot to effect translation of the two sections relative to one another.

23. The implant of claim 22, wherein the distracting mechanism includes a rotatable adjustment, the rotatable adjustment movably housed within the slot and threadably engaging the sliding section to provide controlled translation of the sliding section relative to the slot, thereby providing controlled separation of the respective vertebral osteotomy and expansion of the spinal canal.

24. The implant of claim 20, wherein the dorsal vertebral device includes rounded ends, each rounded end having an adjacent fixation groove, and wherein each connecting device includes a hole at an end thereof for receiving a respective rounded end of the dorsal vertebral device, each connecting device further including a fixation screw perpendicularly aligned thereto to enter the hole and engage the fixation groove of a received dorsal vertebral device, thereby providing secure attachment of the dorsal vertebral device to the two connecting devices in any of a plurality of angular positions between the dorsal vertebral device and each of the two connecting devices to accommodate variations in a local anatomy.

25. The implant of claim 20, wherein the vertebral fixation devices each include a through hole having a longitudinal axis aligned generally perpendicularly to a longitudinal axis thereof, and a locking bolt positioned to enter the through hole and having a longitudinal axis aligned with the longitudinal axis of the vertebral fixation device, the through hole and locking bolt accepting and securing a rod to fix the first vertebra to a second, third or more vertebrae while expanding the spinal canal.

26. An implant for expanding and fixing a spinal canal, comprising:
a dorsal vertebral device that connects to a dorsal vertebral element of a first vertebra, the dorsal vertebral device being a shaft shaped transosseous implant that passes through a tunnel formed in a dorsal vertebral element of the first vertebra;
two vertebral fixation devices that each connect to a vertebral element of the first vertebra more anterior than the dorsal vertebral element;
two connecting devices, each connecting device providing communication between the dorsal vertebral device and a respective one of the two vertebral fixation devices, wherein:
each connecting device connected to the dorsal vertebral device, in use, spans a vertebral osteotomy in the first vertebra, and
each connecting device has a distracting mechanism with two sections that translate relative to one another along an axis generally perpendicular to a longitudinal axis of the respective connecting device, to translate the dorsal vertebral device in a dorsal direction relative to the respective one of the two vertebral fixation devices, whereby the vertebral osteotomies are separated to expand the spinal canal.

27. The implant of claim 26, wherein the dorsal vertebral element is one of a spinous process, lamina, pars intra articularis and articular process of the first vertebra.

28. The implant of claim 26, wherein the connecting device having a distracting mechanism with two sections includes:
   a slot aligned generally perpendicularly to the longitudinal axis of the connecting device; and
   a sliding section movable within the slot to effect translation of the two sections relative to one another.

29. The implant of claim 26, wherein the dorsal vertebral device includes rounded ends, each rounded end having an adjacent fixation groove, and wherein each connecting device includes a hole at an end thereof for receiving a respective rounded end of the dorsal vertebral device, each connecting device further including a fixation screw perpendicularly aligned thereto to enter the hole and engage the fixation groove of a received dorsal vertebral device, thereby providing secure attachment of the dorsal vertebral device to the two connecting devices in any of a plurality of angular positions between the dorsal vertebral device and each of the two connecting devices to accommodate variations in a local anatomy.

* * * * *